US011713400B2

(12) United States Patent
Schulte et al.

(10) Patent No.: US 11,713,400 B2
(45) Date of Patent: Aug. 1, 2023

(54) COMPOSITION FOR PRODUCTION OF COATINGS HAVING AN ANTIMICROBIAL PROPERTY

(71) Applicant: Evonik Operations GmbH, Essen (DE)

(72) Inventors: Simone Schulte, Essen (DE); Markus Hallack, Schermbeck (DE); Sabine Krusenbaum, Essen (DE); Christina Janke, Essen (DE)

(73) Assignee: Evonik Operations GmbH, Essen (DE)

(*) Notice: Subject to any disclaimer, the term of this patent is extended or adjusted under 35 U.S.C. 154(b) by 106 days.

(21) Appl. No.: 17/176,922

(22) Filed: Feb. 16, 2021

(65) Prior Publication Data

US 2021/0253889 A1 Aug. 19, 2021

(30) Foreign Application Priority Data

Feb. 18, 2020 (EP) .................... 20157842

(51) Int. Cl.
*C09D 101/14* (2006.01)
*C09D 133/10* (2006.01)
(Continued)

(52) U.S. Cl.
CPC ............. *C09D 101/14* (2013.01); *C09D 5/14* (2013.01); *C09D 133/10* (2013.01);
(Continued)

(58) Field of Classification Search
CPC ...... C09D 101/14; C09D 5/14; C09D 133/10; C09D 175/06; C09D 179/08; C08K 3/11; C08K 3/08; C08K 3/34
See application file for complete search history.

(56) References Cited

U.S. PATENT DOCUMENTS 8,236,239 B2 8/2012 Bernstein
9,796,876 B2 10/2017 Lomoelder et al.
(Continued)

FOREIGN PATENT DOCUMENTS

CN 105018088 11/2015
CN 108707357 A * 10/2018 ............... C09D 5/22
(Continued)

OTHER PUBLICATIONS

Cates et al., "*Converting Visible Light into UVC: Microbial Inactivation by $Pr^{3+}$-Activated Upconversion Materials*", Environmental Science & Technology, 2011, vol. 45, Issue 8, 7 pages.
(Continued)

*Primary Examiner* — Robert S Jones, Jr.
*Assistant Examiner* — Jiangtian Xu
(74) *Attorney, Agent, or Firm* — Grüneberg and Myers, PLLC

(57) ABSTRACT

A curable composition for production of coatings with an antimicrobial property contains at least one film-forming polymer, at least one up-conversion phosphor, optionally, at least one additive, and optionally, at least one curing agent. The phosphor is selected from the idealized general formula (I), $A_{1-x-y-z}B^*_yB_2SiO_4:Ln^1_x,Ln^2_z$, where x=0.0001-0.05, z=0 or z=0.0001 to 0.3, and y=x+z; A is selected from Mg, Ca, Sr, and Ba; B is selected from Li, Na, K, Rb, and Cs; B* is selected from Li, Na, and K; where B is the same as B* or B is not the same as B*, and B and B* are preferably not the same; $Ln^1$ is selected from praseodymium (Pr), erbium (Er), and neodymium (Nd); and $Ln^2$ is optionally selected from gadolinium (Gd).

24 Claims, 5 Drawing Sheets

(51) Int. Cl.
   *C09D 175/06* (2006.01)
   *C09D 179/08* (2006.01)
   *C09D 5/14* (2006.01)
   *C08K 3/11* (2018.01)
   *C08K 3/08* (2006.01)
   *C08K 3/34* (2006.01)

(52) U.S. Cl.
   CPC ......... *C09D 175/06* (2013.01); *C09D 179/08* (2013.01); *C08K 3/08* (2013.01); *C08K 3/11* (2018.01); *C08K 3/34* (2013.01)

(56) References Cited

U.S. PATENT DOCUMENTS

| | | |
|---|---|---|
| 11,254,819 B2 | 2/2022 | Hallack et al. |
| 2011/0171062 A1 | 7/2011 | Wolfe |
| 2015/0191625 A1 | 7/2015 | Lomoelder et al. |
| 2019/0112502 A1 | 4/2019 | Sloot et al. |
| 2021/0122921 A1 | 4/2021 | Hallack et al. |
| 2022/0325176 A1 | 10/2022 | Schulte et al. |
| 2022/0325177 A1 | 10/2022 | Schulte et al. |

FOREIGN PATENT DOCUMENTS

| | | | |
|---|---|---|---|
| DE | 10 2015 102 427 | 5/2016 | |
| WO | 2009/064845 A2 | 5/2009 | |
| WO | 2009/064845 A3 | 5/2009 | |
| WO | 2018/153437 | 8/2018 | |
| WO | 2019/197076 | 10/2019 | |
| WO | 2021/073914 | 4/2021 | |
| WO | 2021/073915 | 4/2021 | |
| WO | WO-2021073915 A1 * | 4/2021 | ....... C09K 11/77062 |

OTHER PUBLICATIONS

Extended European Search Report dated Sep. 23, 2020 in European Application No. 20157842.4, 8 Pages.
U.S. Appl. No. 16/142,408, filed Sep. 26, 2018, 2019/0112502, Sloot et al.
U.S. Appl. No. 17/658,681, filed Apr. 11, 2022, 2022,0325177, Schulte et al.
U.S. Appl. No. 17/658,664, filed Apr. 11, 2022, 2022/0325176, Schulte et al.

* cited by examiner

COMPOSITION FOR PRODUCTION OF COATINGS HAVING AN ANTIMICROBIAL PROPERTY

CROSS-REFERENCE TO RELATED APPLICATIONS

This application claims priority to European patent application 20157842.4 filed Feb. 18, 2020, incorporated herein by reference.

BACKGROUND OF THE INVENTION

Field of the Invention

The invention relates to a curable composition for production of coatings having an antimicrobial property, to the use thereof and to coatings produced therefrom and articles coated therewith.

Description of Related Art

Every day, humans are exposed to millions of microorganisms such as bacteria, fungi and viruses. Many of these microorganisms are useful or even necessary. Nevertheless, as well as these less harmful representatives, there are also disease-causing or even deadly bacteria, fungi and viruses.

Microorganisms can be transmitted through daily intercourse with other people and contact with articles that have been used by others. Surfaces are given an antimicrobial finish especially in hygiene-sensitive areas. Fields of use are in particular surfaces of medical devices and consumable articles in hospitals, and in outpatient health and welfare facilities. In addition to these, there are surfaces in the public sphere, in the food and drink sector and in animal keeping. The spread of pathogenic microorganisms is a great problem nowadays in the care sector and in medicine, and wherever a large number of humans move in an enclosed space. A particular risk at present is also the increased occurrence of what are called multiresistant bacteria that have become insensitive to standard antibiotics.

In order to reduce the risk of spread of pathogens via contact surfaces, in addition to standard hygiene measures, antimicrobial technologies and materials are being utilized. Chemical substances or the use of physical methods can have a critical influence on the process of propagation of microorganisms. The physical methods include, for example, heat, cold, radiation or ultrasound, etc. Among the chemical methods, halogens, metal ions, organic compounds and dyes, toxic gases, etc., are known.

Even though chemical and physical methods are extremely effective in the destruction of microorganisms in most cases, they have only a short-lived effect, promote the development of resistances and are unsuitable for some applications under some circumstances since they lead to the destruction of the surfaces to be protected. The greatest disadvantage, however, specifically in the case of chemical organic substances, is the hazard or toxicity to man. Particular substances, for example formaldehyde, which found use as disinfectant for many years, are now suspected of causing cancer or of being extremely harmful to the environment.

Surfaces with antimicrobial action could make a crucial contribution to the solution of these problems. The standard processes nowadays for generation of such antimicrobial properties make use predominantly of active ingredients incorporated into the material, for example silver particles, copper particles, metal oxides thereof or quaternary ammonium compounds. This frequently involves processing the antimicrobial metals, metal oxides or metal oxide mixtures to give nanoparticles and then mixing them into paints, coatings or polymer materials. The broad use of metal particles is questionable since it is barely possible to assess the long-term effect of this heavy metal on man and the environment.

For example, WO 2019/197076 discloses particles finished with a layer containing both antimony tin oxide and manganese oxide. The person skilled in the art is aware that the antimicrobial surfaces are produced on account of the electrochemical characteristics of metals which, in the absence of moisture, develop microscale galvanic cells and, by virtue of the microscale electrical fields, germ-killing action.

It is likewise known that UV radiation can be used in medicine or in hygiene, in order, for example, to disinfect water, gases or surfaces. For instance, UV radiation has long been used in drinking water treatment to reduce the number of possibly pathogenic microorganisms in the water. This is preferably done using UV-C radiation in the wavelength range between 100 nm and 280 nm. The use of electromagnetic radiation with different wavelengths should take account of the different absorption of the different proteins, the amino acids/nucleic acids (e.g. DNA) present in microorganisms, tissues or cells, and peptide bonds between the individual acids. For instance, DNA has good absorption of electromagnetic radiation in the wavelength range between 200 nm and 300 nm, and particularly good absorption between 250 nm and 280 nm, and so this radiation is particularly suitable against DNA. It is thus possible to inactivate pathogenic microorganisms (viruses, bacteria, yeasts, moulds inter alia) with such irradiation. According to the duration and intensity of the irradiation, the structure of DNA can be destroyed. Thus, metabolism-active cells are inactivated and/or their replication capacity can be eliminated. What is advantageous about irradiation with UV light is that the microorganisms are unable to develop resistance thereto.

Furthermore, as well as direct irradiation with electromagnetic radiation from the wavelength range of UV light, the exploitation of the effect of what is called up-conversion is also known. This uses phosphor particles with which electromagnetic radiation having wavelengths above UV light, especially visible light or infrared light, can be converted to electromagnetic radiation having shorter wavelength, such that it is possible to achieve the emission of radiation having the desired effect by the individual phosphor particles.

DE 10 2015 102 427 relates to a body that emits electromagnetic radiation in the wavelength range of UV light. Phosphor particles are embedded in the body in a near-surface region within the material from which the body is formed or in a coating on the body. All that is stated here in general terms is that the phosphor particles are added directly to a coating to be formed on the material in the course of processing, where the particular active ingredient should have a suitable consistency or viscosity. DE 10 2015 102 427 is silent with regard to suitable polymers and additives.

US 2009/0130169 A1 and WO 2009/064845 A2 describe phosphors that can be introduced into polyvinylchlorides, acryloylbutadienes, olefins, polycarbonates, styrenes or nylon, which kill pathogenic microorganisms by virtue of the up-conversion property of the phosphors. These are phosphors that are prepared at a temperature of 1800°

C.-2900° C. Furthermore, US 2009/0130169 A1 discloses a liquid composition comprising a polyurethane, an acrylate polymer and fillers, and optionally a crosslinker. US 2009/0130169 A1 addresses the antimicrobial action of the phosphors but does not discuss the compatibility of the component in the coating composition or the properties of the coating surfaces, for instance the paint surfaces. However, the appearance of coating surfaces is paramount for the consumer.

US 2009/0130169 A1 and WO 2009/064845 A2 do disclose a composition comprising said phosphors that is claimed to have antimicrobial action, but there is no evidence of the up-conversion property nor any microbiological studies. The process disclosed therein does not lead to a phosphor that has an up-conversion property, but rather to an amorphous and glassy product.

The demands on paints and coatings are diverse. In principle, paints or coatings have two tasks or functions: the protective and the decorative function. If merely the term "paint coating" should be stated below, both types of coating are intended. They decorate, protect and preserve materials such as wood, metal or plastic. Accordingly, bright and glossy paint layers are required on the one hand, and a continuous coating layer on the other hand for assurance of chemical and mechanical resistance, a certain surface slip of the coatings or a particular haptic property.

SUMMARY OF THE INVENTION

Accordingly, the problem addressed by the present invention is that of providing a curable composition of the type specified at the outset, with which it is possible to produce coatings where long-lasting protection against microorganisms is provided, without significantly impairing the other properties, especially storage stability.

The problem is therefore solved by proposing a curable composition for production of coatings with an antimicrobial property, comprising
   at least one film-forming polymer,
   at least one up-conversion phosphor,
   optionally at least one additive,
   optionally at least one curing agent,
wherein the phosphor is selected from the idealized general formula (I)

$$A_{1-x-y-z}B^*{}_yB_2SiO_4{:}Ln^1{}_x Ln^2{}_z \qquad (I)$$

with
$x=0.0001\text{-}0.05$, $z=0$ or $z=0.0001$ to $0.3$ and $y=x+z$,
A is selected from Mg, Ca, Sr and Ba,
B is selected from Li, Na, K, Rb and Cs,
B* is selected from Li, Na and K, where B is the same as B* or B is not the same as B*, and B and B* are preferably not the same, and
$Ln^1$ is selected from praseodymium (Pr), erbium (Er) and neodymium (Nd),
$Ln^2$ is optionally selected from gadolinium (Gd).

The present invention also includes the following embodiments below:
1. A curable composition for production of coatings with an antimicrobial property, the composition comprising:
   at least one film-forming polymer,
   at least one up-conversion phosphor.
   optionally, at least one additive, and
   optionally, at least one curing agent,
   wherein the at least one phosphor is selected from the idealized general formula (I)

$$A_{1-x-y-z}B^*{}_yB_2SiO_4{:}Ln^1{}_x Ln^2{}_z \qquad (I)$$

with
$x=0.0001\text{-}0.05$, $z=0$ or $z=0.0001$ to $0.3$ and $y=x+z$,
A is selected from Mg, Ca, Sr and Ba,
B is selected from Li, Na, K, Rb and Cs,
B* is selected from Li, Na and K, where B is the same as B* or B is not the same as B*, and B and B* are preferably not the same, and
$Ln^1$ is selected from praseodymium (Pr), erbium (Er) and neodymium (Nd),
$Ln^2$ is optionally selected from gadolinium (Gd).

2. The composition according to embodiment 1, characterized in that the phosphor has been doped with praseodymium.
3. The composition according to either of the preceding embodiments, characterized in that the phosphor has been doped with praseodymium and co-doped with gadolinium.
4. The composition according to any of the preceding embodiments, characterized in that the phosphor is a solidified melt composed of crystalline silicates or of crystalline silicates doped with lanthanoid ions, comprising at least one alkali metal ion and at least one alkaline earth metal ion, preferably in that the crystalline silicates have been doped with praseodymium and optionally co-doped with gadolinium.
5. The composition according to any of the preceding embodiments, characterized in that the phosphor is selected from the idealized general formula (Ia)

$$A_{1-x-y-z}B^*{}_yB_2SiO_4{:}Pr_x Gd_z, \qquad Ia$$

with A=Mg, Ca, Sr, Ba and B=Li, Na, K, Rb, Cs, and
where, in formula Ia, $x=0.0001\text{-}0.05$, $z=0$ or $z=0.0001$ to $0.3$ and $y=x+z$,
B* is selected from Li, Na and K, which serve to balance the charge of the silicates,
where B is the same as B* or B is not the same as B*, and B and B* are preferably not the same.
6. The composition according to any of the preceding embodiments, characterized in that the phosphor is selected from the general formula (II)

$$(Ca_{1-a}Sr_a)_{1-2b}Ln_b Na_b Li_2 SiO_4 \qquad II$$

where
$a=0.0001$ to $1$, preferably $0.0001$ to $0.1$,
$b=0.0001$ to $1$, preferably $0.0001$ to $0.1$,
and Ln=lanthanoid ion selected from praseodymium, gadolinium, erbium, neodymium, and for the co-doping at least one of these, preferably gadolinium.
7. The composition according to any of the preceding embodiments, characterized in that the phosphor which, on irradiation with electromagnetic radiation having lower energy and longer wavelength in the range from 2000 nm to 400 nm, especially in the range from 800 nm to 400 nm, emits electromagnetic radiation having higher energy and shorter wavelength in the range from 400 nm to 100 nm, preferably in the range from 300 nm to 200 nm, where the intensity of the emission maximum of the electromagnetic radiation having higher energy and shorter wavelength is an intensity of at least $1 \cdot 10^3$ counts/(mm$^2$'s), preferably higher than $1 \cdot 10^4$ counts/(mm$^2$*s), more preferably higher than $1 \cdot 10^5$ counts/(mm2*s).
8. The composition according to any of the preceding embodiments, characterized in that the phosphor according to formula (II) has XRPD signals in the range from 23° 2Θ to 27° 2Θ and from 34° 2Θ to 39.5° 2Θ.
9. The composition according to any of the preceding embodiments, characterized in that the film-forming polymer contains functional groups, preferably acidic hydrogens that are reactive with an isocyanate-containing curing agent or with a catalyst.
10. The composition according to any of the preceding embodiments, characterized in that the film-forming polymer is selected from the group of the hydroxy-functional acrylate polymers, hydroxy-functional polyester polymers, and/or hydroxy-functional polyether polymers, hydroxy-functional cellulose derivatives, amino-functional aspartic polymers or polyester polymers, which reacts with an isocyanate-containing curing agent.
11. The composition according to any of the preceding embodiments, characterized in that the film-forming polymer has low resonance.
12. The composition according to any of the preceding embodiments, characterized in that the transmittance of the film-forming polymer is at least 75%, preferably at least 80% and more preferably at least 85%, by means of a twin-beam UV/VIS spectrometer.
13. The composition according to any of the preceding embodiments, characterized in that the transmittance is at least 70%, preferably at least 75% and more preferably at least 80%, by means of a twin-beam UV/VIS spectrometer.
14. The composition according to any of the preceding embodiments, characterized in that the phosphors have an average particle size of d50=0.1-100 μm, preferably d50=1-50 μm, measured to ISO 13320:2020 and USP 429.
15. The composition according to any of the preceding embodiments, characterized in that the additives are selected from the group of the dispersants, rheology aids, levelling agents, wetting agents, defoamers and UV stabilizers.
16. The composition according to any of the preceding embodiments, characterized in that the curing agent is selected from the group of the aliphatic and cycloaliphatic isocyanates.
17. The composition according to any of the preceding embodiments, characterized in that coatings produced therefrom have antimicrobial action against bacteria, yeasts, moulds, algae, parasites and viruses.
18. The composition according to any of the preceding embodiments, characterized in that coatings produced therefrom have antimicrobial action against
pathogens of nosocomial infections, preferably against *Enterococcus faecium, Staphylococcus aureus, Klebsiella pneumoniae, Acinetobacter baumanni, Pseudomonas aeruginosa, Escherichia coli, Enterobacter, Corynebacterium diphteria, Candida albicans*, rotavirus, bacteriophages;
pathogenic environmental organisms, preferably against *Cryptosporidium parvum, Giardia lamblia*, amoebas (*Arcanthamoeba* spp., *Naegleria* spp.), *E. coli*, coliform bacteria, faecal streptococci, *Salmonella* spp., *Shigella* spp., *Leginonella* spec., *Pseudomonas aeruginosa, Mykobakteria* spp., enteral viruses (e.g. polio and hepatitis A virus);
pathogens in food and drink, preferably against *Bacillus cereus, Campylobacter* spp., *Clostridium botulinum, Clostridium perfringens, Cronobacter* spp., *E. coli, Listeria monocytogenes, Salmonella* spp., *Staphylococcus aureus, Vbrio* spp., *Yersinia enterocolitica*, bacteriophages.
19. Use of the composition according to any of the preceding embodiments for production of dispersions, millbases, adhesives, trowelling compounds, renders, paints, coatings or printing inks, inkjets, grinding resins or pigment concentrates.
20. Use of the composition according to any of embodiments 1 to 18 for production of coatings having an antimicrobial property.
21. Use of the composition according to any of embodiments 1 to 18 for coating of substrates in hygiene facilities and hospitals and in the food and drink industry.
22. A process for forming an antimicrobial coating on a substrate, comprising the applying of a curable film-forming composition to the substrate, comprising:
    (a) at least one film-forming polymer containing functional groups reactive with an isocyanate-containing curing agent, optionally catalysed by a catalyst,
    (b) at least one phosphor of the formula (II) and
    (c) a curing agent containing isocyanate-functional groups.
23. The process according to embodiment 22, wherein the substrate comprises metal, mineral substrates, cellulosic substrates, wood and hybrids thereof, dimensionally stable plastics and/or thermosets.
24. The process according to embodiment 22, wherein a primer composition is applied to the substrate prior to the application of the curable film-forming composition.
25. An article, wherein the article has been coated at least partly with the curable composition according to embodiment 1.

DETAILED DESCRIPTION OF THE INVENTION

Figure 1:
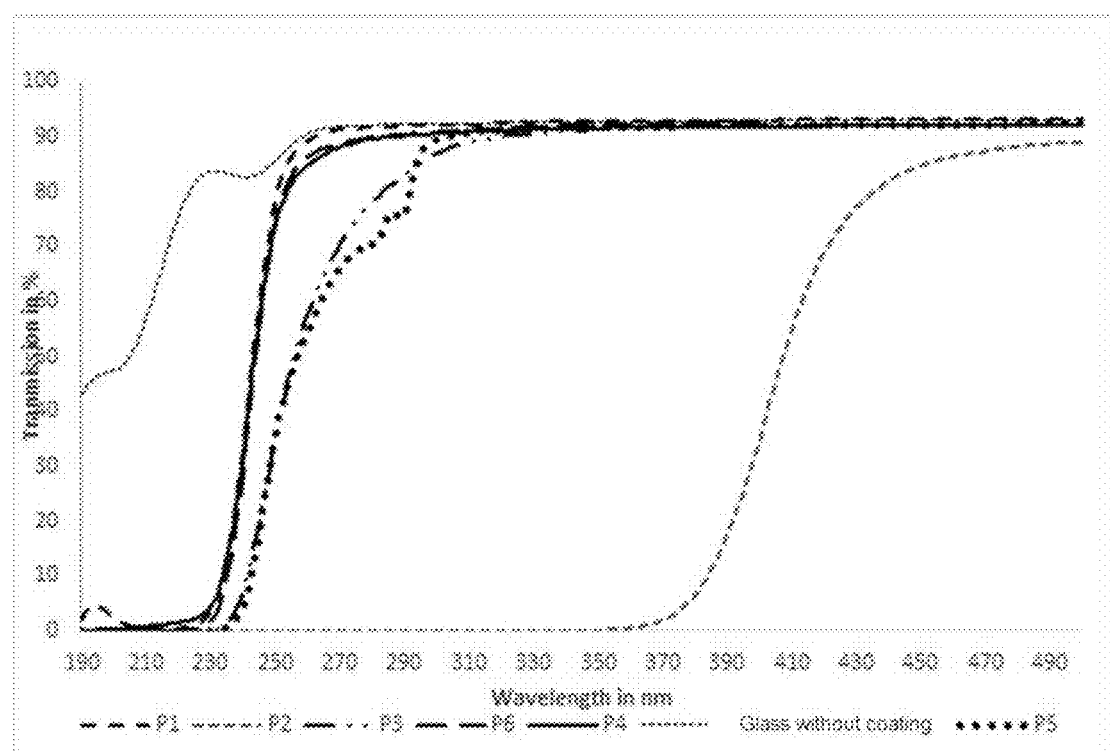
FIG. 1 shows a transmission spectra of the polymer matrices P1-P6 and quartz glass without coating as reference.

It has now been found that, surprisingly, it is possible to use the composition according to the invention to produce coatings having antimicrobial action and no impairment of the surface profile.

The phosphor has preferably been doped with praseodymium, which is used in the composition according to the invention.

For the composition according to the invention, the phosphor has preferably been doped with praseodymium and co-doped with gadolinium.

The phosphor is preferably a solidified melt composed of crystalline silicates or composed of crystalline silicates doped with lanthanoid ions, comprising at least one alkali metal ion and at least one alkaline earth metal ion.

For the composition according to the invention, the phosphor is preferably selected from the idealized general formula (Ia)

$$A_{1-x-y-z}B^*_yB_2SiO_4:Pr_xGd_z \quad \text{(Ia)}$$

with A=Mg, Ca, Sr, Ba and B=Li, Na, K, Rb, Cs, and where, in formula Ia, x=0.0001-0.05, z=0 or z=0.0001 to 0.3 and y=x+z.

B* is selected from Li, Na and K, which serve to balance the charge of the silicates, where B is the same as B* or B is not the same as B*, and B and B* are preferably not the same.

For the composition according to the invention, the phosphor is preferably selected from the general formula (II)

$$(Ca_{1-a}Sr_a)_{1-2b}Ln_bNa_bLi_2SiO_4 \qquad \text{II}$$

where a=0.0001 to 1, preferably 0.0001 to 0.1,
b=0.0001 to 1, preferably 0.0001 to 0.1,
and Ln=lanthanoid ion selected from praseodymium, gadolinium, erbium, neodymium, and for the co-doping at least one of these, preferably gadolinium.

It should be noted here that the phosphors required for the present invention are disclosed from the previously unpublished European patent application having application reference EP 19202910.6.

The phosphor is preferably one which, on irradiation with electromagnetic radiation having lower energy and longer wavelength in the range from 2000 nm to 400 nm, especially in the range from 800 nm to 400 nm, emits electromagnetic radiation having higher energy and shorter wavelength in the range from 400 nm to 100 nm, preferably in the range from 300 nm to 200 nm, where the intensity of the emission maximum of the electromagnetic radiation having higher energy and shorter wavelength is an intensity of at least $1 \cdot 10^3$ counts/(mm$^2$*s), preferably higher than $1 \cdot 10^4$ counts/(mm$^2$*s), more preferably higher than $1 \cdot 10^5$ counts/(mm$^2$*s). The emission spectra are excited by means of a laser, especially a laser having a power of 75 mW at 445 nm and/or a power of 150 mW at 488 nm.

The phosphor of formula (II) preferably has XRPD signals in the range from 23° 2Θ to 27° 2Θ and from 34° 2Θ to 39.5° 2Θ, where the signals are determined by means of the Bragg-Brentano geometry and Cu—Kα radiation. Details of the test method can be found in as yet unpublished European patent application EP 19202910.6.

As yet unpublished European patent application EP 19202910.6 is dedicated to the preparation of phosphors, especially of phosphors of formula (I), formula (Ia) and formula (II). This describes a process comprising the following steps:
i) providing at least one lanthanoid salt selected from lanthanoid nitrates, lanthanoid carbonates, lanthanoid carboxylates, preferably lanthanoid acetates, lanthanoid sulfates, lanthanoid oxides, more preferably $Pr_6O_{11}$ and/or $Gd_2O_3$, where the lanthanoid ion in the lanthanoid oxides or lanthanoid salts is selected from praseodymium, gadolinium, erbium, neodymium and, for co-doping, at least two of these,
ii) providing a silicate, preferably a silicate salt, more preferably an alkali metal salt of the silicate,
iii) providing at least one alkaline earth metal salt and at least one alkali metal salt, preferably an alkali metal silicate selected from a lithium salt or a lithium compound and optionally selected from a sodium salt and potassium salt, preferably the salt of the lithium salt and is a lithium silicate,
a) mixing i), ii) and iii) by means of grinding to obtain a mixture, or
b) mixing i), ii) and iii) in an organic polar or nonpolar solvent that is not a protic solvent to obtain a mixture; the mixture from b) is calcined (step 1a) at 600° C. to 1000° C. to remove the organic component; preference is given to performing the calcining at 600° C. to 1000° C. for at least 1 h, preferably not less than 2 h, under normal (air) atmosphere to obtain a calcined mixture, calcining the mixture from a) or the calcined mixture from b) in a calcining step, preferably under air at a temperature below the melting temperature of the silicate-based material, wherein at least partial crystallization takes place, preferably in a further calcining step (step 1b) at a temperature of 50 to 200° C. for at least 3 h, preferably under air, below the melting temperature of the silicate-based material, in order to crystallize the silicate-based material, preferably at a temperature of 800 to 900° C., more preferably at about 850° C., for at least 3 h, preferably for at least 12 h, preferably under air, in a further calcination step with rising temperature, preferably above 800° C. and 50 to 200° C. below the melting point (step 2) of the material, for example at 850° C. for at least 3 h, more preferably for at least 6 h, under reduced atmosphere, reducing the lanthanoids to $Ln^{3+}$ ions, obtaining a silicate-based lanthanoid ion-doped material, preferably after cooling the material.

Further detailed embodiments of the process can be found in EP 19202910.6.

It has been found that, surprisingly, the phosphors according to EP 19202910.6 have the required up-conversion properties responsible for antimicrobial action. In other words, these phosphors can convert electromagnetic radiation having wavelengths above UV light, especially visible light or infrared light, to electromagnetic radiation having shorter wavelength, specifically in the region in which, for example, the DNA of the microorganisms can be destroyed. Accordingly, these phosphors are of very good suitability for the composition according to the invention.

Preparation of the phosphor according to the invention is also conceivable as follows:

Starting materials used are $CaCO_3$ (Alfa Aesar, 99.5%), $Li_2CO_3$ (Alfa Aesar, 99%), $SiO_2$ (Aerosil 200, Evonik), $Pr_6O_{11}$ (Treibacher, 99.99%), and $Na_2CO_3$ (Merck, 99.9%). A stoichiometric mixture of these compounds is mixed in acetone for 30 minutes. Once acetone has fully evaporated at room temperature, the mixture is transferred to a corundum crucible. The mixture is calcined twice. The first calcination is performed in a melting furnace at 850° C. for 12 h with supply of air, and the second calcination at 850° C. under 95/5 $N_2/H_2$ for 6 h. The end product is subsequently ground in an agate mortar.

A further problem addressed by the invention is the selection of film-forming polymers that can be used for the curable composition having an antimicrobial property. In principle, all film-forming polymers known from the prior art are useful.

The film-forming polymer preferably has functional groups, preferably acidic hydrogens that are reactive with an isocyanate-containing curing agent, and is optionally catalysed by a catalyst.

Advantageously, the film-forming polymer is selected from the group of the hydroxy-functional acrylate polymers, hydroxy-functional polyester polymers, and/or hydroxy-functional polyether polymers, hydroxy-functional cellulose derivatives, amino-functional aspartic polymers or polyester polymers, which reacts with an isocyanate-containing curing agent.

The film-forming polymer preferably has low resonance.

The person skilled in the art is aware of the physical interactions at the surface. According to the material and its material surface, a multitude of effects occur at the surface on incidence of light. The incident light is partly absorbed, partly reflected and, according to the material surface, also scattered. Light can also first be absorbed and then emitted again. In the case of opaque, semitransparent or transparent materials, the light can also penetrate through the body (transmittance). In some cases, the light is even polarized or diffracted at the surface. Some objects can even emit light (illuminated displays, LED segments, displays), or fluoresce or phosphoresce in light of a different colour (afterglow).

What is meant by "low resonance" in the context of this invention is that the film-forming polymer has low absorption, reflection, reflectance and scatter. By contrast, transmittance should preferably be pronounced.

This is because it has possibly been found that, surprisingly, the film-forming polymers according to the invention that have low resonance have improved antimicrobial action, because more electromagnetic radiation having lower energy and higher wavelength in the range from 2000 nm to 400 nm, especially in the range from 800 nm to 400 nm, is transmitted and, as a result, they can emit more electromagnetic radiation having higher energy and shorter wavelength in the range from 400 nm to 100 nm, preferably in the range from 300 nm to 200 nm.

It has been found that the higher the transmittance, the higher the emission as well, which is crucial for antimicrobial action.

The transmittance of the film-forming polymer is preferably at least 75%, more preferably at least 80% and especially preferably at least 85%, measured at a wavelength of 260 nm.

The transmittance of the film-forming polymer is preferably at least 75%, more preferably at least 80% and especially preferably at least 85%, measured at a wavelength of 500 nm. By way of illustration, it should be noted here that transmittance may be defined at a different wavelength; see FIG. 1. For the present invention, the wavelengths of 260 nm by way of example for the wavelength emitted and 500 nm by way of example for the excitation wavelength were chosen, which are responsible firstly for the up-conversion and secondly to a significant degree for the antimicrobial action.

In the case of 100% transmittance, for example, measured at a wavelength of 260 nm, the same amount of radiation is converted and emitted; in other words, there are no losses through absorption, scatter or the like. In the case of transmittance of 80%, measured at a wavelength of 260 nm, 20% is not transmitted, probably owing to absorption, reflection, reflectance and/or scatter. Accordingly, only 80% of the radiation of wavelength 260 nm can be emitted.

This significant finding is important in the selection of the film-forming polymers. Polymers having 0% transmittance, for example, are unsuitable for the curable composition according to the invention. They do not transmit any electromagnetic radiation having lower energy and higher wavelength and, accordingly, phosphors present in the composition cannot convert this electromagnetic radiation to electromagnetic radiation having higher energy and shorter wavelength and emit it, which is required for antimicrobial action.

Preferably, the composition according to the invention has a transmittance of at least 75%, preferably at least 80% and more preferably at least 85%, measured at 260 nm.

Preferably, the composition according to the invention has a transmittance of at least 75%, preferably at least 80% and more preferably at least 85%, measured at 500 nm.

The transmittances are preferably measured with a "Specord 200 Plus" twin-beam UV/VIS spectrometer from Analytik Jena. A holmium oxide filter is used for internal wavelength calibration. Monochromatic light from a deuterium lamp (UV range) or a tungsten-halogen lamp (visible range) is passed through the samples. The spectral bandwidth is 1.4 nm. The monochromatic light is divided into a measurement channel and a reference channel and enables direct measuring against a reference sample. The radiation transmitting through the sample is detected by a photodiode and processed.

It is conceivable to use a composition having a transmittance of less than 70%; they possibly also have antimicrobial action, but the efficiency is very moderate.

The phosphors preferably have an average particle size of d50 of 0.1-100 μm, preferably d50=1-50 μm, measured to ISO 13320:2020 and USP 429, for example with an instrument from Horiba, LA-950 Laser Particle Size Analyzer.

In order to efficiently incorporate and/or to stabilize the phosphors in the composition according to the invention, it is preferably possible to add various additives.

The additives are preferably selected from the group of the dispersants, rheology aids, levelling agents, wetting agents, defoamers and UV stabilizers.

It has been found that, surprisingly, any addition of additives to the composition according to the invention reduces transmittance.

Accordingly, the composition according to the invention, in a further embodiment in which additives are used, preferably has a transmittance of at least 70%, preferably at least 75% and more preferably at least 80%, measured at 260 nm.

Accordingly, the composition according to the invention, in a further embodiment in which additives are used, preferably has a transmittance of at least 70%, preferably at least 75% and more preferably at least 80%, measured at 500 nm.

Preferably, the composition according to the invention includes a curing agent selected from the group of the aliphatic or cycloaliphatic isocyanates.

Examples of isocyanate-containing curing agents are monomeric isocyanates, polymeric isocyanates and isocyanate prepolymers. Polyisocyanates are preferred over monomeric isocyanates on account of their lower toxicity. Examples of polyisocyanates are 30 isocyanurates, uretdiones and biurets based on diphenylmethane diisocyanate (MDI), toluene diisocyanate (TDI), hexamethylene diisocyanates (HDI) and isophorone diisocyanate (IPDI). Examples of commercially available products are under the trade name DESMODUR® from Covestro or VESTANAT from Evonik Industries. Known products are DESMODUR® N3400, DESMODUR® N3300, DESMODUR® N3600 DESMODUR® N75, DESMODUR® XP2580, DESMODUR® Z4470, DESMODUR® XP2565 and DESMODUR® VL from Covestro. Further examples are VESTANAT® HAT 2500 LV, VESTANAT® HB 2640 LV or VESTANAT® T 1890E from Evonik Industries. Examples of isocyanate prepolymers are DESMODUR® E XP 2863, DESMODUR® XP 2599 or DESMODUR® XP 2406 from Covestro. Further isocyanate prepolymers known to those skilled in the art may be used.

It is conceivable to use catalysts for curing. The catalysts that follow, selected from organic Sn(IV), Sn(II), Zn, Bi compounds or tertiary amines, may be used.

Preference is given to using catalysts selected from the group of organotin catalysts, titanates or zirconates, organometallic compounds of aluminium, iron, calcium, magnesium, zinc or bismuth, Lewis acids or organic acids/bases, linear or cyclic amidines, guanidines or amines or a mixture thereof.

Curing catalysts used are preferably organic tin compounds, for example, dibutyltin dilaurate, dibutyltin diacetylacetonate, dibutyltin diacetate, dibutyltin dioctoate, or dioctyltin dilaurate, dioctyltin diacetylacetonate, dioctyltin diketanoate, dioctylstannoxane, dioctyltin dicarboxylate, dioctyltin oxide, preferably dioctyltin diacetylacetonate, dioctyltin dilaurate, dioctyltin diketanoate, dioctylstannoxane, dioctyltin dicarboxylate, dioctyltin oxide, more preferably dioctyltin diacetylacetonate and dioctyltin dilaurate. In addition, it is also possible to use zinc salts, such as zinc octoate, zinc acetylacetonate and zinc-2-ethylcaproate, or tetraalkylammonium compounds, such as N,N,N-trimethyl-N-2-hydroxypropylammonium hydroxide, N,N,N-trimethyl-N-2-hydroxypropylammonium 2-ethylhexanoate or choline 2-ethylhexanoate. Preference is given to the use of zinc octoate (zinc 2-ethylhexanoate) and of the tetraalkylammonium compounds, particular preference to that of zinc octoate. Further preferred are bismuth catalysts, e.g. TIB Kat (TIB Mannheim) or Borchi® catalysts, titanates, e.g. titanium(IV) isopropoxide, iron(III) compounds, e.g. iron(III) acetylacetonate, aluminium compounds, such as aluminium triisopropoxide, aluminium tri-sec-butoxide and other alkoxides and also aluminium acetylacetonate, calcium compounds, such as calcium disodium ethylenediaminetetraacetate or calcium diacetylacetonate, or else amines, examples being triethylamine, tributylamine, 1,4-diazabicyclo[2.2.2]octane, 1,8-diazabicyclo[5.4.0]undec-7-ene, 1,5 diazabicyclo[4.3.0]non-5-ene, N,N-bis(N,N-dimethyl-2-aminoethyl)methylamine, N,N-dimethylcyclohexylamine, N,N dimethylphenylamine, N-ethylmorpholine, etc. Also preferred as catalysts are organic or inorganic Brønsted acids such as acetic acid, trifluoroacetic acid, methanesulfonic acid, p-toluenesulfonic acid or benzoyl chloride, hydrochloric acid, phosphoric acid and the monoesters and/or diesters thereof, for example butyl phosphate, (iso)propyl phosphate, dibutyl phosphate, etc. Also preferred are guanidine-bearing organic and organosilicon compounds. It is of course also possible to use combinations of two or more catalysts. In addition, it is also possible to use photolatent bases as catalysts, as described in WO 2005/100482.

The curing catalyst is preferably used in amounts of 0.01% to 5.0% by weight, more preferably 0.05% to 4.0% by weight and especially preferably 0.1% to 3% by weight based on the total mass of the curable composition.

In the case of film-forming polymers that cure through physical drying, the addition of reactive curing agents is not required.

The compositions according to the invention may preferably be used in 1K (one-component) coating systems or 2K (two-component) coating systems, in melamine baking systems, or room- or high-temperature systems.

Preferably, coatings produced from the composition according to the invention have antimicrobial action against bacteria, yeasts, moulds, algae, parasites and viruses.

The coatings produced according to the invention preferably have antimicrobial action against
pathogens of nosocomial infections, preferably against *Enterococcus faecium, Staphylococcus aureus, Kebsiella pneumoniae, Acinetobacter baumannii, Pseudomonas aeruginosa, Escherichia coli, Enterobacter, Corynebacterium diphteria, Candida albicans*, rotavirus, bacteriophages: facultative pathogenic environmental organisms, preferably against *Cryptosporidium parvum, Giardia lamblia*, amoebas (*Arcanthamoeba* spp., *Naegleria* spp.), *E. coli*, coliform bacteria, faecal streptococci. *Salmonella* spp., *Shigella* spp., *Leginonella* spec., *Pseudomonas aeruginosa, Mykobakteria* spp., enteral viruses (e.g. polio and hepatitis A virus); pathogens in food and drink, preferably against *Bacillus cereus, Campylobacter* spp., *Clostridium botulinum, Clostridium perfingens, Cronobacter* spp., *E. coli, Listeria monocytogenes, Salmonella* spp. *Staphylococcus aureus, Vibrio* spp., *Yersinia enterocolitica*, bacteriophages.

The invention further provides for the use of the composition according to the invention for production of dispersions, millbases, adhesives, trowelling compounds, renders, paints, coatings or printing inks, inkjets, grinding resins or pigment concentrates.

Preference is given to the use of the composition according to the invention for production of coatings having an antimicrobial property.

What is meant here by a coating having antimicrobial action or an antimicrobial property is that the coating has an antimicrobial surface that limits or prevents the growth and proliferation of microorganisms.

It has also been found that, astonishingly, the coatings according to the invention have chemical and mechanical stability. Chemical and mechanical stability is particularly important since antimicrobial coatings are frequently used in areas that require regular disinfection and further hygiene measures.

The invention also includes a method for forming an antimicrobial coating on a substrate, comprising the applying of a curable film-forming composition to the substrate, comprising:
a. at least one film-forming polymer containing functional groups reactive with an isocyanate-containing curing agent, optionally catalysed by a catalyst,
b. at least one phosphor of the formula (II) and
c. a curing agent containing isocyanate-functional groups.

Preferably, the substrate comprises metal, mineral substrates (for instance concrete, natural rock or glass), cellulosic substrates, wood and hybrids thereof, or dimensionally stable polymers and/or thermosets.

The term "dimensionally stable polymers" is understood to mean, albeit non-conclusively, the following polymers: acrylonitrile-butadiene-styrene (ABS), polyamides (PA), polylactate (PLA), polymethylmethacrylate (PMMA), polycarbonate (PC), polyethylene terephthalate (PET), polystyrene (PS), polyetheretherketone (PEEK), polyvinylchloride (PVC), polypropylene (PP), polyethylene (PE).

Preferably, a primer composition may be applied to the substrate prior to the application of the curable film-forming composition.

Preferably, the curable composition according to the invention is used for the coating of substrates in hygiene facilities and hospitals and in the food and beverage industry.

This may include all settings in public sectors, for example schools, old people's homes, industrial kitchens or nurseries.

A further invention is the article coated at least partly, preferably fully, with the curable composition according to the invention.

It should be noted here that the terms "antimicrobial effect", "antimicrobial efficacy", "antimicrobial action" and "antimicrobial property" are used as synonyms.

Indicated hereinafter are examples that serve solely to elucidate this invention to the person skilled in the art and do not constitute any restriction at all of the subject-matter claimed.

Methods

Measurement of Transmittance

The measurements of transmittance were determined with a "Specord 200 Plus" twin-beam UV/VIS spectrometer from Analytik Jena. A holmium oxide filter is used for internal wavelength calibration. Monochromatic light from a deuterium lamp (UV range) or a tungsten-halogen lamp (visible range) was passed through the samples. The spectral bandwidth is 1.4 nm. The monochromatic light is divided into a measurement channel and a reference channel and enables direct measuring against a reference sample. The radiation transmitting through the sample is detected by a photodiode and processed. The measurements were effected in transmission mode. The measurement range was 190 to 1100 nm with a step width of 1 nm. The measurement speed was 10 nm/s, corresponding to an integration time of 0.1 s.

Instruments

Speedmixer, from Hauschild Engineering, model FAC 150.1 FVZ

Dispermat, from Getzmann, instrument type CV2-SIP

Reflectometer, from Zehntner Testing Instruments, instrument type ZGM 1130

Cross-cut tester, DIN EN ISO 2409, MTV Messtechnik oHG, type: CCP cross-cut stencil set Erichsen cupping test, from Erichsen, 202 type MEK twin-stroke test, from Bruno Pellizzato, type: Tester Veslic Type Rotary viscometer, from Anton Paar, instrument: Viskotherm VT 2

Spectrophotometer (for the measurement of colour locus determination), from X-Rite, instrument type SP 62

Laboratory balance, Sartorius MSE 6202 S 100 DO

Haemocytometer (Thoma counting chamber): from Brandt

Agitated waterbath: GFL 1083, from Byk Gardner

Specord 200 Plus twin-beam UV/VIS spectrometer, from Analytik Jena

Nutrient Media

Caso broth: from Merck KGaA Millipore

CASO nutrient agar plates: from Oxoid

Disinfectant

Bacillol® AF: from Hartmann

Materials

TABLE 1

Overview of raw materials for the polymer matrices used

| Trade name | Chemical composition | Use | Company |
|---|---|---|---|
| Degalan® 64/12 | Air-drying linear polyacrylate | Film-forming polymer | Evonik |
| Polyimide P84®NT | Polyimide resin | Film-forming polymer | Evonik |
| Desmophen® NH 1420 | Polyaspartic resin | Film-forming polymer | Covestro |
| Dynacoll® AC 3820 | Hydroxyl-containing linear polyacrylate | Film-forming polymer | Evonik |
| Setal® 1603 | Hydroxyl-containing polyester | Film-forming polymer | Alinex |
| CAB™ 381-2 | Cellulose ester | Film-forming polymer | Eastman |
| Desmodur® N 3390 | Polyisocyanate | Curing agent | Covestro |
| Butyl acetate | Butyl acetate | Solvent | Sigma-Aldrich |
| TIB KAT® 218 | Dibutyltin dilaurate | Catalyst | TIB Chemicals AG |

TABLE 2

Overview of the additives used

| Trade name | Chemical composition | Use | Company |
|---|---|---|---|
| TEGO® Dispers 710 | Solution of a basic urethane copolymer | Dispersant | Evonik |
| TEGO® Dispers 628 | Solution of a high molecular weight polymer | Dispersant | Evonik |
| TEGO® Dispers 670 | Solution of a high molecular weight polymer | Dispersant | Evonik |
| TEGO® Dispers 650 | Modified polyether having groups with pigment affinity | Dispersant | Evonik |
| TEGO® Dispers 652 | Concentrate of a fatty acid derivative | Dispersant | Evonik |
| TEGO® Dispers 630 | Solution of a high molecular weight acrylic acid polymer with amine derivative | Dispersant | Evonik |
| TEGO® Dispers 688 | High molecular weight polymer | Dispersant | Evonik |
| TEGO® Dispers 689 | High molecular weight polymer | Dispersant | Evonik |
| TEGO® Dispers 1010 | High molecular weight polymer | Dispersant | Evonik |
| SPHERILEX® DP0111 | Synthetic amorphous silica | Filler | Evonik |
| SPHERILEX® DP0112 | Synthetic amorphous silica | Filler | Evonik |
| AEROSIL® R 972 | Fumed silica | Filler | Evonik |
| AEROSIL® 200 | Fumed silica | Filler | Evonik |
| BENTONE® SD-2 | Bentonite, sheet silicate | Filler | Elementis |
| BENTONE® SD-3 | Hectorite, sheet silicate | Filler | Elementis |
| BENTONE® 38 | Modified hectorite, sheet silicate | Filler | Elementis |
| SPHERILEX™ DP0115 | Synthetic amorphous silica | Filler | Evonik |

FIGURES

FIG. 1: Transmission spectra of the polymer matrices P1-P6 and quartz glass without coating as reference FIG. 2: Construction of the agar plate test.

The phosphor sample (▒) is applied to a confluently inoculated nutrient agar plate (▓) and incubated at room temperature under constant illumination for 24±1 h. To verify the antimicrobial efficacy through the effect of the up-conversion, the samples were additionally incubated in the dark.

Figure 3:
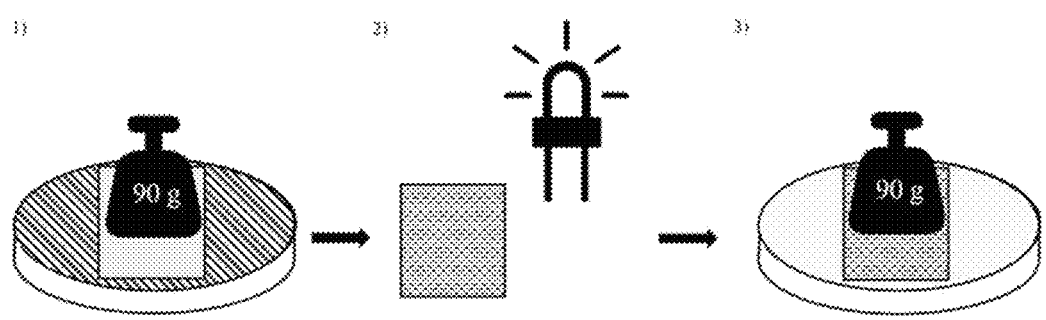
FIG. 3 shows a construction of the transfer method.

FIG. 3: Construction of the transfer method.

The polymeric matrices with the phosphors present are pressed onto a confluently inoculated nutrient agar plate with a defined weight (1). The bacteria transferred thereby are incubated at room temperature under illumination or in the dark (2). The antimicrobial effect is detected by direct contact of the samples on nutrient agar under defined weight (3).

Figure 4:
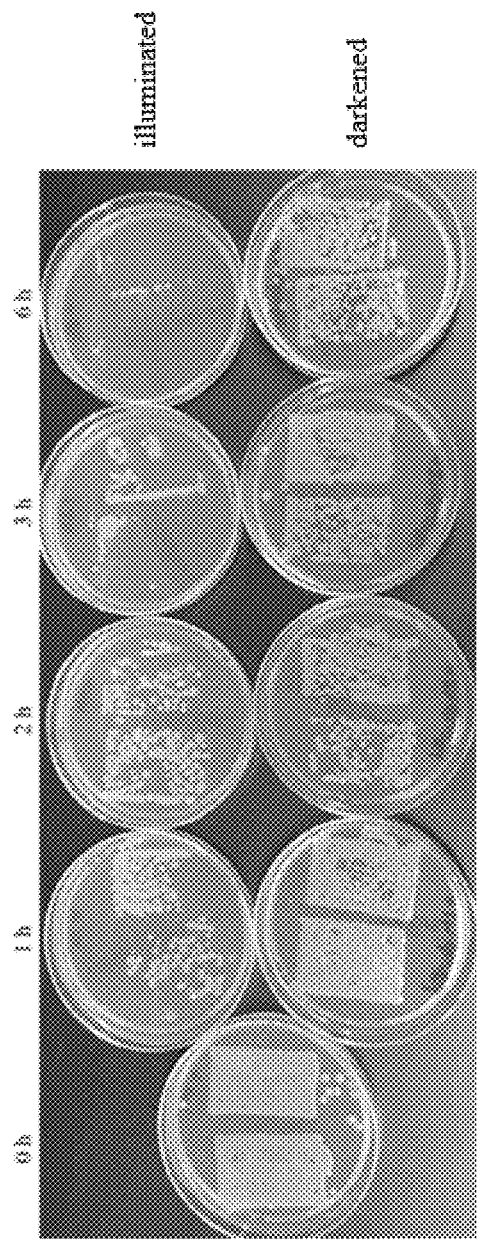
FIG. 4 shows a representative photograph of the culturability of *B. subtilis* after incubation on the polymeric matrix with $CaLi_2SiO_4:Pr^{3+}$, $Na^+$(1%) in the illuminated and darkened state.

FIG. 4: Culturability of B. subtilis after incubation on the polymeric matrix with $CaLi_2SiO_4:Pr^{3+},N^+(1\%)$ in the illuminated and darkened state. B. subtilis was incubated at room temperature, with and without illumination, for 0 h, 1 h, 2 h, 3 h and 6 h. The subsequent culturing of the cells on CASO agar was done at 30° C. for 24±1 h. The figure shows a representative photograph.

Figure 5:
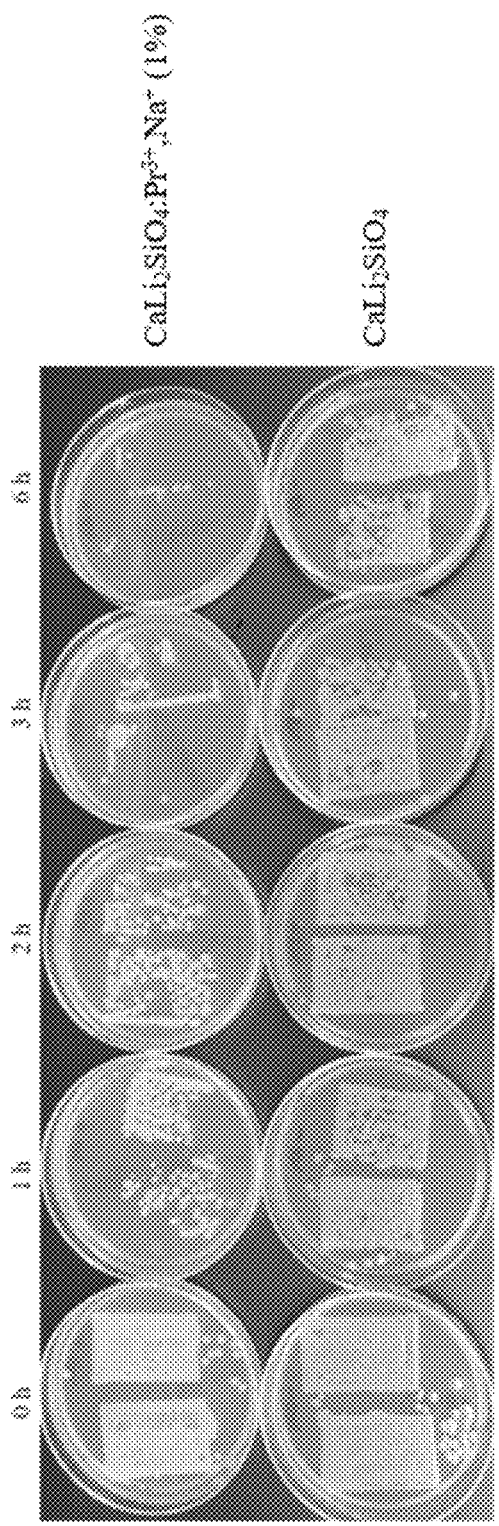
FIG. 5 shows a representative photograph of the culturability of *B. subtilis* after incubation on the polymeric matrix with $CaLi_2SiO_4:Pr^{3+}$, $Na^+$(1%) and $CaLi_2SiO_4$ in the illuminated state.

FIG. 5: Culturability of B. subtilis after incubation on the polymeric matrix with $CaLi_2SiO_4:Pr^{3+},Na^+(1\%)$ and $CaLi_2SiO_4$ in the illuminated state. B. subtilis was incubated at room temperature with constant illumination for 0 h, 1 h, 2 h, 3 h and 6 h. The subsequent culturing of the cells on CASO agar was done at 30° C. for 24±1 h. The figure shows a representative photograph.

1. Selection of the Film-Forming Polymers

Using the transmittance measured, the suitable film-forming polymers for the composition according to the invention were selected.

1.1 Preparation of the Composition without Phosphors and Additives

Polymer matrices P1-P6 were produced as follows, where P1 and P2 are a 1-component system that dries physically. P3-P6 are chemically curing 2-component systems.

The polymers from Table 1 were diluted or dissolved in butyl acetate in the amounts listed in Table 3. (Exception: Polyimide P84® NT, which was used in neat form). Subsequently, 20 g of this polymer solution was weighed into 50 ml plastic cups. The curing agent and/or catalyst was added only shortly prior to application. The polymer matrices were then homogenized in a Speedmixer at 2000 rpm for 1 min.

TABLE 3

Composition of 100 g of each of polymer matrices P1-P6

| Raw materials [g] | P1 | P2 | P3 | P4 | P5 | P6 |
|---|---|---|---|---|---|---|
| Degalan ® 64/12 | 73.2 | | | | | |
| Polyimide P84 ®NT | | 100 | | | | |
| Desmophen ® NH 1420 | | | 44.2 | | | |
| Dynacoll ® AC 3820 | | | | 32.2 | | |
| Setal ® 1603 | | | | | 54.9 | |
| CAB ™ 381-2 | | | | | | 27.2 |
| Desmodur ® N 3390 | | | 33.6 | 4 | 31.2 | 9.1 |
| Butyl acetate | 26.8 | | 22.1 | 63.70 | 13.8 | 63.6 |
| TIB KAT ® 218 | | | 0.1 | 0.1 | 0.1 | 0.1 |

1.2 Coating of the Polymer Matrices onto Quartz Plates

P1-P6 were applied to quartz plates with a suitable spiral coater, so as to achieve a dry layer thickness of 30 µm in the dried state. These were dried/cured at room temperature (23° C.) for 10 days.

1.3 Measurement of Transmittance

Subsequently, the UV/VIS transmission spectrum was measured.

Polymer matrices P1, P4 and P6 show high transmission in the wavelength range of 450 to 500 nm (blue light) and 250 to 300 nm (UV-C/B light) (FIG. 1), and Table 4 shows the transmittances at a wavelength of 260 nm and 500 nm.

P1, P4 and P6 have a transmittance of greater than 80% at both wavelengths. Thus, it is possible to use the film-forming polymers Degalan® 64/12 (in P1), Dynacoll® AC 3820 (in P4) and CAB™ 381-2P6 (in P6) for the composition according to the invention for production of coatings having an antimicrobial property. Polyimide P84®NT in P2 can serve as comparative polymer since this polymer has zero transmittance at the wavelength of 260 nm.

TABLE 4

Overview of transmittance at 260 nm and 500 nm

| Polymer matrix | Transmittance 260 nm [%] | Transmittance 500 nm [%] |
|---|---|---|
| P1 | 89.45 | 93.3 |
| P2 | 0 | 89.2 |
| P3 | 57.72 | 92.4 |
| P4 | 84.85 | 92.2 |
| P5 | 54.45 | 92.4 |
| P6 | 86.31 | 92.8 |

2. Selection of Additives

For optimization of the coating properties and stabilization of the phosphors, for example against settling in the liquid composition according to the invention, various additives were tested in the polymer matrix P4. As well as the functional suitability of the additives, the suitability thereof with regard to their effect on transmittance was tested. For this purpose, UV/VIS transmittance spectra of the formulations of various additives in the polymer matrix P4 were measured.

2.1 Measurement of Transmittance

For this purpose, 20 g of polymer matrix P4 and the amount of the additive to be tested were weighed out (see Table 5) and homogenized in a Speedmixer at 2000 rpm for 1 min. Shortly prior to the application, curing agent and catalyst were added and the mixture was homogenized once again in the Speedmixer at 2000 rpm for 1 min. These mixtures P4-1 to P4-17 were applied to quartz glass plates and aluminium sheets with a spiral applicator and dried/cured at room temperature for 10 days. They were tested for their transmittance and coating properties.

With reference to the UV/VIS transmittance spectra, the additives TEGO® Dispers 628, TEGO® Dispers 670. TEGO® Dispers 688, SPHERILEX® DP0111, SPHERILEX® DP0112, SPHERILEX® DP0115, AEROSIL® R 972, AEROSIL® 200, BENTONE SD®-2, BENTONE SD®-3 and BENTONE® 38 are suitable for the composition according to the invention since they do not significantly reduce the required transmittance, even with regard to the transmittance of the film-forming polymers (see Table 2). The transmittances thereof are greater than 70%.

Transmittances less than 70% were able to be measured for the additives TEGO® Dispers 710, TEGO® Dispers 650, TEGO® Dispers 652. TEGO® Dispers 630, TEGO® Dispers 689 and TEGO® Dispers 1010. (Table 5).

TABLE 5

Overview of the UV/IS transmittance [%] of the composition composed of the film-forming polymer P4 with additives at 260 nm and 500 nm.

| | Additive product name | Amount of the additive [g] | Transmittance 260 nm [%] | Transmittance 500 nm [%] |
|---|---|---|---|---|
| P4 | | none | 84.85 | 92.2 |
| P4-1 | TEGO ® Dispers 710 | 2.86 | 0.4 | 84.41 |
| P4-2 | TEGO ® Dispers 628 | 2 | 79.49 | 91.7 |
| P4-3 | TEGO ® Dispers 670 | 2.5 | 72.39 | 92.72 |
| P4-4 | TEGO ® Dispers 650 | 1 | 51.11 | 92.62 |
| P4-5 | TEGO ® Dispers 652 | 1 | 35.52 | 92.3 |
| P4-6 | TEGO ® Dispers 630 | 2 | 47.77 | 86.02 |
| P4-7 | TEGO ® Dispers 688 | 2.2 | 79.49 | 92.62 |
| P4-8 | TEGO ® Dispers 689 | 2.2 | 55.79 | 89.64 |
| P4-9 | TEGO ® Dispers 1010 | 1 | 69.84 | 85.05 |
| P4-10 | SPHERILEX ® DP0111 | 0.4 | 75.2 | 88.25 |
| P4-11 | SPHERILEX ® DP0112 | 0.4 | 77.89 | 89.21 |
| P4-12 | AEROSIL ® R 972 | 0.4 | 82.49 | 92.06 |
| P4-13 | AEROSIL ® 200 | 0.4 | 84.28 | 92.51 |
| P4-14 | BENTONE SD ®-2 | 0.4 | 76.72 | 91.24 |
| P4-15 | BENTONE SD ®-3 | 0.4 | 74.59 | 91.11 |
| P4-16 | BENTONE ® 38 | 0.4 | 77.93 | 91.22 |
| P4-17 | SPHERILEX ® DP0115 | 0.4 | 77.18 | 89.04 |

2.2 Testing of the Coating Properties of the Polymer Matrices without Phosphors

The liquid polymer matrices were applied with a spiral applicator to bonder 26 s 6800 OC sheets and dried/cured at 23° C. for 10 days. A final dry layer thickness of 30 μm was achieved.

The following coating properties were verified in accordance with standard DIN and ISO standards:
Gloss
König pendulum hardness
Cross-cut test
Erichsen cupping test
MEK twin-stroke test
Chemical stability to ketchup, coffee, sulfuric acid (50% solution in water), sodium hydroxide solution (10% solution in water) and suncream. The suncream, after being applied to the surface of the coating, was subjected to 60° C. in an oven for 1 h; all the other chemicals remained at room temperature for 16 h before they were removed and then the damage to the surface of the coating was assessed.

Bacillol twin-stroke test: Bacillol® AF is suitable for rapid disinfection of alcohol-resistant surfaces by a spraying/wiping method.

The coating properties were tested in polymer matrices P3-P6 (Table 6). It was found that polymer matrices P4 and P6 satisfy the typical coating properties. These can therefore be used for the further tests.

TABLE 6

Coating properties of P3 to P6

| Test | Standard | Basis for assessment | Tolerance/customary values | P4 | P5 | P3 | P6 |
|---|---|---|---|---|---|---|---|
| König pendulum hardness | DIN EN ISO 1522 | Impacts | Soft: <90 Hard: >140 | 112 | 157 | 141 | 127 |
| Gloss at 20° | DIN EN ISO 2813 | Units | High gloss: at 20° > 70U Semi-gloss: at 60° 10-70U | 88 | 86.8 | 91.1 | 97 |
| Cross-cut | DIN EN ISO 2409 | Visual: scale from 0 to 5 | 0 = no flaking 5 = flaked off completely | 0 | 5 | 5 | 0 |
| Erichsen cupping | DIN EN ISO 1520 | mm | Hard: <2 mm Soft: >6 mm | 2 | 2 | 4.8 | 2 |
| MEK test | ASTM D 4752 | Twin strokes | Low crosslinking density: <50 High crosslinking density: >200 | 113 | >200 | >200 | >200 |
| Bacillol test | In accordance with ASTM D 4752 | Twin strokes | Low crosslinking density: <50 High crosslinking density: >200 | >200 | >200 | >200 | >200 |
| Resistance to ketchup | DIN EN ISO 175 | Visual: scale from 1 to 10 | 1 = significant change 10 = no change | 10 | 10 | 10 | 10 |
| Resistance to coffee | DIN EN ISO 175 | Visual: scale from 1 to 10 | 1 = significant change 10 = no change | 10 | 10 | 10 | 10 |
| Resistance to $H_2SO_4$ (50% in water) | DIN EN ISO 175 | Visual: scale from 1 to 10 | Insignificant change 10 = no change | 10 | 10 | 10 | 10 |
| Resistance to NaOH (10% in water) | DIN EN ISO 175 | Visual: scale from 1 to 10 | Insignificant change 10 = no change | 10 | 10 | 10 | 10 |

3. Testing of Antimicrobial Efficacy 3.1 Selection of Phosphors

The following phosphors were used:
$Lu_2CaAl_4SiO_{12}:Pr^{3+},Gd^{3+}$, prepared according to unpublished European patent application EP 19202897.5, Example 6
$CaLi_2SiO_4:Pr^{3+},Na^+$(1%), prepared according to unpublished European patent application EP 19202910.6, Example 1

CaLi$_2$SiO$_4$, prepared according to unpublished European patent application EP 19202910.6, Example 1, without using praseodymium.

Li$_4$P$_2$O$_7$, prepared by the following method:

1.8473 g (25.0000 mmol) of Li$_2$O$_3$ and 2.8756 g (25.000 mmol) of NH$_4$H$_2$PO$_4$ were mixed in acetone in an agate mortar. This prepared mixture was calcined under normal (air) atmosphere at 500° C. for 6 h. Calcination was effected under normal (air) atmosphere at 650° C. for a further 12 h to obtain the product.

BaY$_2$SI$_3$O$_{10}$:Pr$^{3+}$, prepared by the following method:

2.1273 g (10.7800 mmol) of BaCO$_3$, 1.9828 g (33.0000 mmol) of SiO$_2$, 2.4839 g (11.0000 mmol) and 0.0187 g (0.0183 mmol) of PreO were mixed in acetone in an agate mortar. This prepared mixture was calcined under a CO atmosphere at 1400° C. for 6 h to obtain the product.

Ca$_3$Sc$_2$Si$_3$O$_{12}$:Pr$^{3+}$,Na$^+$(1%), prepared by the following method:

1.8119 g (18.1030 mmol) of CaCO$_3$, 0.0104 g (0.0102 mmol) of Pr$_6$O$_{11}$, 0.8428 g (6.1110 mmol) of Sc$_2$O$_3$ and 0.0032 g (0.0306 mmol) of Na$_2$CO$_3$ were dissolved in hot concentrated nitric acid. The solution was concentrated in order to obtain the nitrates. Water was added to the nitrates while stirring constantly. 1.1043 g (18.3790 mmol) of SiO$_2$ was mixed with 20 ml of water and placed in an ultrasound bath to separate the agglomerates. This dispersion was fed into the above-mentioned water/nitrate solution and mixed. 11.1314 g (121.1300 mmol) of C$_4$H$_{11}$NO$_3$ was added thereto. The solution was concentrated. The reaction product was dried at 150° C. Then the reaction product was calcined under normal (air) atmosphere in a muffle furnace at 1000° C. for 2 h. A further calcination step was conducted at 1300° C. under a forming gas (N$_2$/H$_2$; 95%/5%) for 4 h to obtain the product.

The phosphor was prepared in accordance with WO 2009/064845 A2:

3.3349 g (33.3200 mmol) of CaCO$_3$, 2.5123 g of (34.0000 mmol) LiCO$_3$, 0.1479 g (0.3400 mmol) of Pr(NO$_3$)$_3$·6H$_2$O and 0.0180 g (0.1700 mmol) of Na$_2$CO$_3$ are mixed in hexane in an agate mortar. Na$_2$CO$_3$ was added to compensate for the charge of Ca$^{2+}$/Pr$^{3+}$. This mixture was calcined at 700° C. with supply of air for removal of organic constituents for two hours. Subsequently, the calcination is conducted at 1100° C. (or higher) for 12 h, which led to an amorphous and glassy product that stuck fast in the crucible. It was not possible to separate the amorphous product from the Al$_2$O$_3$ crucible.

Thus, the phosphor according to WO 2009/064845 A2 is unsuitable for the composition according to the invention. This was not usable for the further studies.

3.2 Testing of the Antimicrobial Efficacy of the Phosphors

First of all, the antimicrobial efficacy of the phosphors as such was tested. The efficacy of the phosphors was tested against Gram-positive and Gram-negative test organisms.

Testing was effected on *Bacillus subtilis*, which is used for biodosimetric testing of UV systems in DVGW (German Technical and Scientific Association for Gas and Water) Arbeitsblatt W 294 "UV-Geräte zur Desinfektion in der Wasserversorgung" [Standard W 294 "UV Instruments for Disinfection in Water Supply"]. Being a Gram-positive spore-forming bacterium, it is particularly insensitive to UV radiation and hence of good suitability as a worst case for testing of the antimicrobial action of UV radiation.

In addition, antimicrobial efficacy was tested on *Escherichia coli*, in order to show antimicrobial action against Gram-negative bacteria. E coil is a Gram-negative aerobic bacterium that occurs predominantly in the human intestinal tract and is thus a typical indicator of faecal contamination. In the event of contamination of other tissues with *E. coli*, the result is frequently infection diseases, for example infections in the urogenital tract.

3.2.1 Agar Plate Test

Using the agar plate test, the antimicrobial action of phosphors on the test organisms *B. subtilis* and *E. coli* was verified.

Figure 2:
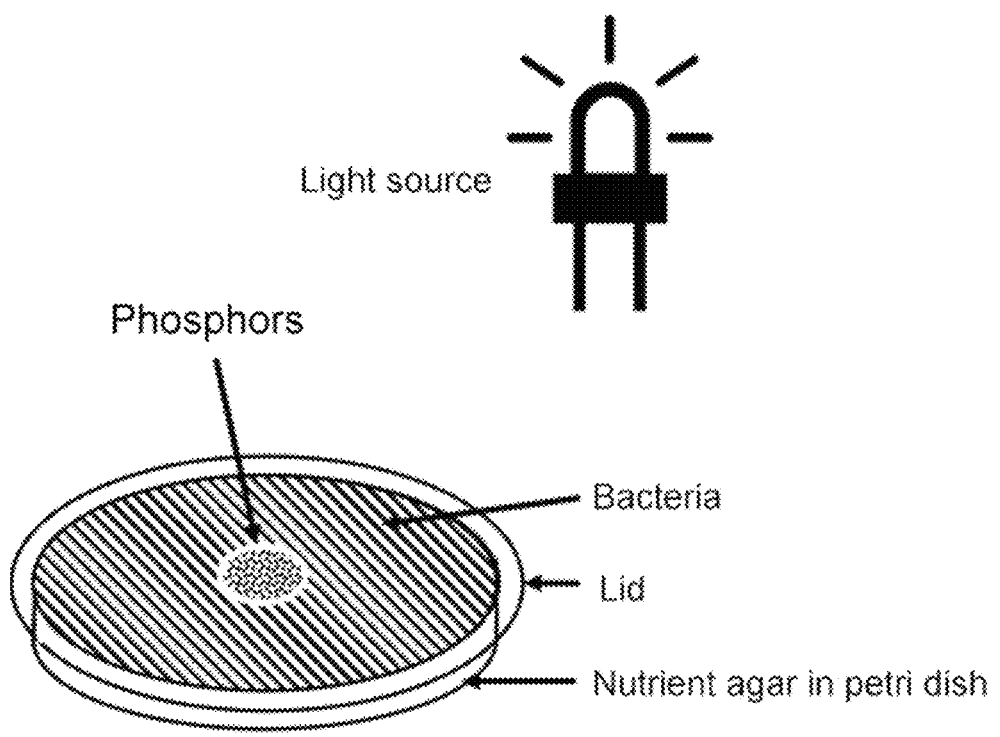
FIG. 2 shows a construction of the agar plate test.

For testing, solid nutrient agar plates were confluently inoculated with a bacteria suspension of the test organisms. The phosphor samples were applied to the inoculated nutrient plates (FIG. 2). The plates were incubated under suitable growth conditions. After the plates have been incubated, the growth-inhibiting properties were assessed from the formation of a zone without colony growth concentrically at and around the accumulated phosphors on the nutrient plates.

The test organisms used were *Bacillus subtilis* subsp. *spizizenii* (DSM 347, ATCC 6633) and *Escherichia coli* (DSM 1116; ATCC 9637). The test organisms were used in suspension with a final concentration of 10$^7$ cells/mi.

The bacteria suspensions were produced by dilutions of pre-cultures of the respective bacterial strain. Dilution was effected in sterile deionized water. The pre-cultures of the test organisms were produced in sterilized casein peptone-soya flour peptone (CASO) broth. The pre-culture of *B. subtilis* was incubated at 30° C. with constant agitation in an agitated waterbath for 16±1 h. The pre-culture of *E. coli* was incubated at 36° C. in a thermally insulated Erlenmeyer flask with a magnetic stirrer bar with constant stirring at 350 rpm. The cell titre of the pre-cultures was determined by microscopy with a haemocytometer (Thoma counting chamber).

For the agar plate test, 1.0 ml of the bacteria suspension with 10$^7$ cells/mi was distributed homogeneously over a sterile CASO agar plate in order to assure confluent coverage of the nutrient agar. The bacteria suspension applied was equilibrated on the nutrient agar at room temperature (22±2° C.) for 300±30 sec before the phosphors were applied centrally. In addition, calcium carbonate and copper oxide were each also applied centrally to the nutrient plates as negative and positive reference. It is known that copper oxides have a growth-inhibiting effect, whereas calcium carbonates must not show any growth-inhibiting effect.

The nutrient plates were incubated under constant illumination at room temperature for 24±1 h. The same preparation was additionally also incubated in the dark.

Incubating under illumination and in the dark, if there is any growth-inhibiting effect only in the illuminated state, should indicate the up-conversion property of the phosphors.

All samples and references were tested in triplicate and with and without illumination over the incubation period of 24±1 h.

Phosphors and phosphor particles are used as synonyms.

3.2.2 Results of the Agar Plate Test

The growth-inhibiting effect of the phosphors on bacteria was detected visually after 24±1 h at room temperature (Table 7).

There is a growth-inhibiting effect when a concentric zone without bacterial colony growth arises around and at the accumulated phosphor particles or reference particles on the nutrient agar.

There is no growth-inhibiting effect when bacterial colony growth is detected on the nutrient agar around and at the accumulated phosphor particles or reference particles.

After incubation under illumination after 24±1 h at room temperature, it was possible to detect a growth-inhibiting effect of the phosphor CaLi$_2$SiO$_4$:Pr$^{3+}$,Na$^+$(1%) for *B. subtilis* and *E. coli*. It was not possible to detect any growth-inhibiting effect around the other phosphors (Table 7).

For all phosphors, it was not possible to detect any bacterial colony growth under the darkened incubation conditions around and at the accumulated phosphor particles.

These results show clearly that the reason for the antimicrobial action of the phosphors CaLi$_2$SiO$_4$:Pr$^{3+}$,Na$^+$(1%) is the physical effect of the UV emission in the light-excited state.

In the darkened state, no up-conversion takes place, and so no antimicrobial action of the phosphors was detectable in the darkened state.

It is additionally found that the phosphor CaLi$_2$SiO$_4$ did not show any growth-inhibiting effect on the test organisms. Accordingly, it is possible to draw the conclusion, but without being bound to a theory, that the doping of the phosphors with praseodymium is advantageous for the physical effectiveness of the up-conversion of the phosphors.

The reference with calcium carbonate did not show any zone with bacterial growth inhibition either under light or dark conditions. By contrast, the reference with copper oxide shows a concentric zone without bacterial colony growth both under light and dark conditions.

The phosphors additionally did not show any genuine bacterial contamination.

The results show that the phosphor CaLi$_2$SiO$_4$:Pr$^{3+}$,Na$^+$(1%) is suitable for the curable composition according to the invention.

3.3.1 Production of a Curable Composition

The curable compositions Z4-2 and Z6-2 according to the invention and the comparative examples VZ4-1, VZ4-3, VZ2-1, VZ2-2, VZ2-3, VZ6-1 and VZ6-3 were produced according to the details from Table 8. 50 g of glass beads was added to the respective composition and the mixture was ground in a Speedmixer at 2000 rpm for 5 min. After the glass beads had been filtered off, the respective composition was applied to a polymer film and crosslinked to form a film. There is then a coating on the substrate, the coating surface of which should have an antimicrobial effect.

The formulation of the compositions is apparent from Table 8.

3.3.2 Transfer Method

The test organism used was again *Bacillus subtilis* subsp. *spizizenii* (DSM 347, ATCC 6633). 1 ml of a *B. subtilis* suspension with a final concentration of 10$^7$ cells/ml was distributed homogeneously over a sterile CASO agar plate in order to assure confluent coverage of the nutrient agar. The bacterial suspension applied was equilibrated on the nutrient agar at room temperature (22±2° C.) for 300±30 sec. The bacterial suspensions were produced by dilutions of pre-cultures of the respective bacterial strain. Dilution was effected in sterile deionized water. The pre-cultures of the test organisms were produced in a sterilized CASO broth. The pre-culture of *B. subtilis* was incubated at 30° C. with constant agitation in an agitated waterbath for 16±1 h. The cell titre of the pre-cultures was determined by microscopy with a haemocytometer (Thoma counting chamber).

The aim of the transfer method is to simulate the antimicrobial action of the coating surface under close-to-real conditions on a dry inanimate surface. For this purpose, the coatings obtained as described above were cut to a size of 2.5 cm×4 cm and pressed onto a nutrient agar plate confluently inoculated with *B. subtilis* with a defined weight of 90±1 g for 60±5 sec. This step transferred the bacteria in semi-dry form to the surface of the coating. Subsequently, the substrates were placed into an empty petri dish with the coated and inoculated side upward and incubated under illumination at room temperature for 0 h, 1 h, 2 h, 3 h, 6 h.

For testing of the antimicrobial efficacy through the up-conversion effect, the substrates with the coated and inoculated side were additionally also incubated in the dark at room temperature for 0 h, 1 h, 2 h, 3 h, 6 h.

TABLE 7

Results of the agar plate test

| Phosphor | Growth-inhibiting effect on *B. subtilis* | | Growth-inhibiting effect on *E. coli* | |
| --- | --- | --- | --- | --- |
| | Illuminated | Darkened | Illuminated | Darkened |
| Lu$_2$CaAl$_4$SiO$_{12}$:Pr$^{3+}$, Gd$^{3+}$ | No | No | No | No |
| CaLi$_2$SiO$_4$:Pr$^{3+}$, Na$^+$(1%) | Yes | No | Yes | No |
| CaLi$_2$SiO$_4$ | No | No | No | No |
| Li$_4$P$_2$O$_7$ | No | No | No | No |
| BaY$_2$SI$_3$O$_{10}$:Pr$^{3+}$ | No | No | No | No |
| Ca$_3$Sc$_2$Si$_3$O$_{12}$: Pr$^{3+}$, Na$^+$ | No | No | No | No |
| Calcium carbonatereference | No | No | No | No |
| Copper oxide reference | Yes | Yes | Yes | Yes |

3.3 Testing of the Antimicrobial Efficacy of a Composition According to the Invention It was shown under 3.2 that the phosphor CaLi$_2$SiO$_4$:Pr$^{3+}$, Na$^+$(1%) as such has an antimicrobial effect. But whether this antimicrobial effect still pertains in the composition according to the invention is now to be ascertained.

It should be noted here that the terms "antimicrobial effect". "antimicrobial efficacy", "antimicrobial action" and "antimicrobial property" are used as synonyms.

For testing of the antimicrobial efficacy of the composition according to the invention, three phosphors and the film-forming polymer matrices P4, P2 and P6 are used, with P2 serving as comparative example.

The phosphors CaLi$_2$SiO$_4$:Pr$^{3+}$,Na$^+$(1%), Lu$_2$CaAl$_4$SiO$_{12}$:Pr$^{3+}$,Gd$^{3+}$ and CaLi$_2$SiO$_4$ were used, with only CaLi$_2$SiO$_4$:Pr$^{3+}$,Na$^+$(1%) functioning as phosphor according to the invention.

Control references selected were again calcium carbonate (with no growth-inhibiting effect) and copper oxide (with a growth-inhibiting effect).

All samples and references were tested in triplicate and with and without illumination over the incubation period.

The antimicrobial effect after the appropriate incubation time is detected via the determination of culturability by a contact test (FIG. 3).

For the testing of the culturability of *B. subtilis*, the substrates, after the incubation time of 0 h, 1 h, 2 h, 3 h, 6 h, were pressed by the coated and inoculated side on a sterile nutrient agar plate with a defined weight of 90±1 g for 60±5 sec. The nutrient agar was then incubated under static conditions at 30° C. for 24±1 h. The bacterial colonies formed were qualitatively assessed visually.

coll® AC 3820 and the polymer CAB™ 381-2, is not a suitable film-forming polymer for the curable composition according to the invention.

In the reference with calcium carbonate, it was not possible to detect a reduction in the culturability of *B. subtilis* in the illuminated or darkened state. By addition of copper oxide, it was possible to detect a distinct reduction in culturability both in the darkened and in the illuminated state.

The polymeric matrices additionally did not show any genuine contamination.

FIG. 5 shows here too that the phosphor $CaLi_2SiO_4$ does not have any antimicrobial action.

TABLE 8

Formulations of the curable compositions for the transfer method

| | VZ4-1 [g] | Z4-2 [g] | VZ4-3 [g] | VZ2-1 [g] | VZ2-2 [g] | VZ2-3 [g] | VZ6-1 [g] | Z6-2 [g] | VZ6-3 [g] |
|---|---|---|---|---|---|---|---|---|---|
| Dynacoll ® AC 3820 | 16.00 | 16.00 | 16.00 | | | | | | |
| Polyimide P84 ®NT | | | | 50.00 | 50.00 | 50.00 | | | |
| CAB ™ 381-2 | | | | | | | 6.82 | 6.82 | 6.82 |
| Butyl acetate | 32.00 | 32.00 | 32.00 | | | | 38.64 | 38.64 | 38.64 |
| $Lu_2CaAl_4SiO_{12}:Pr^{3+}, Gd^{3+}$ | 1.33 | | | 1.33 | | | 0.90 | | |
| $CaLi_2SiO_4:Pr^{3+}, Na^+(1\%)$ | | 1.33 | | | 1.33 | | | 0.90 | |
| $CaLi_2SiO_4$ | | | 1.33 | | | 1.33 | | | 0.90 |
| TIB Kat ® 218 | 0.03 | 0.03 | 0.03 | | | | 0.05 | 0.05 | 0.05 |
| Desmodur ® N 3390 | 2.00 | 2.00 | 2.00 | | | | 4.55 | 4.55 | 4.55 |

3.3.3 Results of the Transfer Method

Any growth-inhibiting effect can be checked in the transfer method by a decrease in the culturability of *B. subtilis*.

The culturability of adherent bacteria on the coating surface of Z4-2 and Z6-2 showed a distinct reduction in growth with increasing incubation time (FIG. 4). The phosphor $CaLi_2SiO_4:Pr^{3+},Na^+(1\%)$ in the curable composition according to the invention brings about a significant decrease in the culturability of *B. subtilis* compared to the blank sample and the samples incubated in the dark. This reduction was measurable under constant illumination even after incubation for 1 h. The decrease in culturability increases until the incubation time of 6 h under constant illumination. The compositions incubated in the dark did not show any reduction in culturability over the incubation period of 6 h. Representative images are shown in FIG. 4 for Z4-2.

By virtue of the unchanged number of culturable bacteria over the period of 6 h, it is possible to show that the antimicrobial effect of the phosphor exists only in the illuminated state. The up-conversion effect thus exists here too.

The comparative phosphors $Lu_2CaAl_4SiO_{12}:Pr^{3+},Gd^{3+}$ and $CaLi_2SiO_4$ did not show antimicrobial efficacy in any of the comparative compositions, either in the illuminated or darkened state (Table 9).

No antimicrobial effect for the phosphors tested was detectable in the case of comparative composition VZ2-2 (Table 9). It is possible to infer from this that the polymer Polyimide P84® NT, by contrast with the polymer Dyna-

TABLE 9

Antimicrobial efficacy of the curable compositions

| | Antimicrobial effect | |
|---|---|---|
| Composition | Illuminated | Darkened |
| VZ4-1 | No | No |
| Z4-2 | Yes | No |
| VZ4-3 | No | No |
| VZ2-1 | No | No |
| VZ2-2 | No | No |
| VZ2-3 | No | No |
| VZ6-1 | No | No |
| Z6-2 | Yes | No |
| VZ6-3 | No | No |
| Calcium carbonate reference | No | No |
| Copper oxide reference | Yes | Yes |

4. Physical Properties of the Composition According to the Invention

An important property of curable compositions is storage stability. A conclusion as to storage stability can be drawn by measuring the viscosity and characterization of the sediment, such as homogenization and formation of a serum of the curable composition Z4-2 according to the invention as per Table 8, without using any curing agent or any catalyst. Referred to hereinafter as Z4-2*. The phosphor $CaLi_2SiO_4:Pr^{3+},Na^+(1\%)$ was used.

Viscosity

The viscosity of Z4-2*, without curing agent and catalyst, with the respective additives was measured by means of a cone-plate rotary viscometer. The difference in viscosity from the initial value, directly after mixing, was checked after a period of 1 week and 2 weeks at 40° C. (Table 10).

It has been found that all compositions with additives showed improved stability in terms of viscosity on storage at 40° C. compared to the composition without additive. The greater stability with regard to viscosity on storage at 40° C. was exhibited by composition Z4-2* and Tego® Dispers 688. The initial viscosity is even reduced slightly, and guarantees good storage stability.

Sedimentation and Homogenization

In addition, the formation of a sediment was checked after a period of 1 week and 2 weeks at 40° C. (Table 11).

Evaluation Criteria:

Sediment [%]=height [cm] of the sediment compared to the total height [cm] of the wet coating Homogenization=light or heavy, the mixture was stirred here with a spatula.

As can be seen from Table 11, the composition Z4-2* and Tego® Dispers 688 and Z4-2* and Tego® Dispers 670 showed very good results with regard to the sedimentation of particles. No measurable sedimentation of the particles takes place within 2 weeks at 40° C. In the case of Z4-2* and Tego® Dispers 628, the particles were readily homogenizable again after a period of 1 week, which was not the case for the composition without additive.

B is selected from Li, Na, K, Rb, and Cs,
B* is selected from Li, Na, and K,
where B is the same as B* or B is not the same as B*,
$Ln^1$ is selected from the group consisting of praseodymium, erbium, and neodymium, and
$Ln^2$ is optionally gadolinium.

2. The composition according to claim 1, wherein the at least one phosphor has been doped with praseodymium.

3. The composition according to claim 1, wherein the at least one phosphor has been doped with praseodymium and co-doped with gadolinium.

4. The composition according to claim 1, wherein the at least one phosphor is a solidified melt composed of crystalline silicates or of crystalline silicates doped with lanthanoid ions, comprising at least one alkali metal ion and at least one alkaline earth metal ion.

5. The composition according to claim 1, wherein the at least one phosphor is selected from the formula (Ia)

$$A_{1-x-y-z}B^*_yB_2SiO_4:Pr_xGd_z \quad (Ia)$$

wherein
A=Mg, Ca, Sr, or Ba,
B=Li, Na, K, Rb, or Cs,
x=0.0001-0.05, z=0 or z=0.0001 to 0.3, and y=x+z,
B* is selected from Li, Na, and K, which serve to balance the charge of the silicates, and
where B is the same as B* or B is not the same as B*.

TABLE 10

Viscosities [mPa]

| Additive | Additive content [% solids] | Viscosity [mPa] after mixing (t = 0 week) | Δ viscosity [mPa] t = 1 week at 40° C. | Δ viscosity [mPa] t = 2 weeks at 40° C. |
|---|---|---|---|---|
| Z4-2* | 0 | 9489 | +1512.9 | +5803.9 |
| 24-2* and Tego ® Dispers 628 | 5 | 237 | +69.79 | +144.92 |
| Z4-2* and Tego ® Dispers 670 | 5 | 3605 | +248.9 | +552.7 |
| 24-2* and Tego ® Dispers 688 | 5 | 4517 | −191.6 | −201.8 |

TABLE 11

Sedimentation and homogenization

| Additive | Additive content [% solids] | Sedimentation [%] t = 1 week at 40° C. | Homogenization t = 1 week at 40° C. | Sedimentation [%] t = 2 weeks at 40° C. | Homogenization t = 2 weeks |
|---|---|---|---|---|---|
| 24-2* | 0 | 5 | heavy | 5 | heavy |
| Z4-2* and Tego ® Dispers 628 | 5 | 5 | light | 5 | heavy |
| 24-2* and Tego ® Dispers 670 | 5 | No sedimentation | | No sedimentation | |
| 24-2* and Tego ® Dispers 688 | 5 | No sedimentation | | No sedimentation | |

The invention claimed is:

1. A curable composition for production of coatings with an antimicrobial property, the composition comprising:
    at least one film-forming polymer,
    at least one up-conversion phosphor,
    optionally, at least one additive, and
    optionally, at least one curing agent,
    wherein the at least one up-conversion phosphor is selected from the formula (I)

$$A_{1-x-y-z}B^*_yB_2SiO_4:Ln^1_xLn^2_z \quad (I)$$

wherein
x=0.0001-0.05, z=0 or z=0.0001 to 0.3, and y=x+z,
A is selected from Mg, Ca, Sr, and Ba, 6. A curable composition for production of coatings with an antimicrobial property, the composition comprising:
    at least one film-forming polymer,
    at least one up-conversion phosphor,
    optionally, at least one additive, and
    optionally, at least one curing agent,
wherein the at least one phosphor is selected from the formula (II)

$$(Ca_{1-a}Sr_a)_{1-2b}Ln_bNa_bLi_2SiO_4 \quad (II)$$

wherein
a=0.0001 to 1,
b=0.0001 to 1,

Ln=a lanthanoid ion selected from the group consisting of praseodymium, gadolinium, erbium, and neodymium, and wherein at least one of these is provided for co-doping.

7. The composition according to claim 1, wherein the at least one phosphor which, on irradiation with electromagnetic radiation having lower energy and longer wavelength in the range from 2000 nm to 400 nm, emits electromagnetic radiation having higher energy and shorter wavelength in the range from 400 nm to 100 nm, where the intensity of the emission maximum of the electromagnetic radiation having higher energy and shorter wavelength is an intensity of at least $1 \cdot 10^3$ counts/(mm$^2$*s).

8. The composition according to claim 6, wherein the at least one phosphor according to formula (II) has XRPD signals in the range from 23° 2Θ to 27° 2Θ and from 34° 2Θ to 39.5° 2Θ.

9. The composition according to claim 1, wherein the at least one film-forming polymer contains functional groups.

10. The composition according to claim 1, wherein the at least one film-forming polymer is selected from the group consisting of hydroxy-functional acrylate polymers, hydroxy-functional polyester polymers, hydroxy-functional polyether polymers, hydroxy-functional cellulose derivatives, and amino-functional aspartic polymers or polyester polymers, which reacts with an isocyanate-containing curing agent.

11. The composition according to claim 1, wherein a transmittance of the at least one film-forming polymer is at least 75%, by means of a twin-beam UV/VIS spectrometer.

12. The composition according to claim 1, wherein a transmittance of the composition is at least 70%, by means of a twin-beam UV/VIS spectrometer.

13. The composition according to claim 1, wherein the at least one phosphor has an average particle size of d50=0.1-100 μm, measured to ISO 13320:2020 and USP 429.

14. The composition according to claim 1, wherein the at least one additive is present, and wherein the at least one additive is selected from the group consisting of dispersants, rheology aids, levelling agents, wetting agents, defoamers, and UV stabilizers.

15. The composition according to claim 1, wherein the at least one curing agent is present, and wherein the at least one curing agent is selected from the group consisting of aliphatic and cycloaliphatic isocyanates.

16. The composition according to claim 1, wherein coatings produced therefrom have antimicrobial action against bacteria, yeasts, moulds, algae, parasites, and viruses.

17. The composition according to claim 1, wherein coatings produced therefrom have antimicrobial action against pathogens of nosocomial infections, pathogenic environmental organisms, and pathogens in food and drink.

18. A method for production of a dispersion, millbase, adhesive, trowelling compound, render, paint, coating, printing ink, inkjet, grinding resin, or pigment concentrate, the method comprising:
mixing the composition according to claim 1 into the dispersion, millbase, adhesive, trowelling compound, render, paint, coating, printing ink, inkjet, grinding resin, or pigment concentrate.

19. A method for production of coatings having an antimicrobial property, the method comprising:
mixing the composition according to claim 1 into a coating composition.

20. A method for coating substrates in hygiene facilities, hospitals, and in the food and drink industry, the method comprising:
applying a coating composition comprising the composition according to claim 1, to the substrates.

21. A process for forming an antimicrobial coating on a substrate, the process comprising:
applying a curable film-forming composition according to claim 1, to the substrate, wherein the curable film-forming composition comprises
(a) at least one film-forming polymer containing functional groups reactive with an isocyanate-containing curing agent, optionally catalysed by a catalyst,
(b) at least one phosphor of formula (II), and
(c) a curing agent containing isocyanate-functional groups.

22. The process according to claim 21, wherein the substrate comprises metal, mineral substrates, cellulosic substrates, wood and hybrids thereof, dimensionally stable plastics, and/or thermosets.

23. The process according to claim 21, wherein a primer composition is applied to the substrate prior to the application of the curable film-forming composition.

24. An article, wherein the article has been coated at least partly with the curable composition according to claim 1.

* * * * *